US008035175B2

(12) United States Patent
Shim et al.

(10) Patent No.: US 8,035,175 B2
(45) Date of Patent: Oct. 11, 2011

(54) FIELD EFFECT TRANSISTOR FOR DETECTING IONIC MATERIAL AND METHOD OF DETECTING IONIC MATERIAL USING THE SAME

(75) Inventors: Jeo-young Shim, Yongin-si (KR); Kyu-sang Lee, Yongin-si (KR); Kyu-tae Yoo, Yongin-si (KR); Won-seok Chung, Yongin-si (KR)

(73) Assignee: Samsung Electronics Co., Ltd. (KR)

( * ) Notice: Subject to any disclaimer, the term of this patent is extended or adjusted under 35 U.S.C. 154(b) by 197 days.

(21) Appl. No.: 11/613,258

(22) Filed: Dec. 20, 2006

(65) Prior Publication Data
US 2007/0252176 A1    Nov. 1, 2007

(30) Foreign Application Priority Data
Apr. 26, 2006   (KR) .................. 10-2006-0037723

(51) Int. Cl.
*H01L 27/14* (2006.01)
(52) U.S. Cl. .. 257/414; 257/225; 257/253; 257/E29.325
(58) Field of Classification Search .................. 257/213, 257/E51.045, 249, 318, 326, 448; 435/4, 435/287.1, 287.2
See application file for complete search history.

(56) References Cited

U.S. PATENT DOCUMENTS

| | | | |
|---|---|---|---|
| 4,238,757 A | 12/1980 | Schenck | |
| 4,269,682 A | 5/1981 | Yano et al. | |
| 4,288,806 A * | 9/1981 | Ronen | 257/409 |
| 4,411,741 A | 10/1983 | Janata | |
| 4,777,019 A | 10/1988 | Dandekar | |
| 5,466,348 A | 11/1995 | Holm-Kennedy | |
| 5,846,708 A | 12/1998 | Hollis et al. | |
| 6,001,697 A * | 12/1999 | Chang et al. | 438/299 |
| 6,017,775 A * | 1/2000 | Igel et al. | 438/48 |
| 6,203,981 B1 | 3/2001 | Ackley et al. | |
| 6,535,545 B1 * | 3/2003 | Ben-Bassat et al. | 375/142 |
| 2007/0012922 A1 * | 1/2007 | Harada et al. | 257/66 |
| 2008/0063566 A1 * | 3/2008 | Matsumoto et al. | 422/68.1 |

FOREIGN PATENT DOCUMENTS
WO    2005022142    3/2005

OTHER PUBLICATIONS
Olthuis et al., "Dynamic Behaviour of ISFET-based Sensor-Actuator Systems", 1999, pp. 416-420.*

(Continued)

*Primary Examiner* — Evan Pert
*Assistant Examiner* — Eduardo A Rodela
(74) *Attorney, Agent, or Firm* — Cantor Colburn LLP

(57) ABSTRACT

A field effect transistor for detecting ionic material and a method of detecting ionic material using the field effect transistor. The field effect transistor for detecting ionic material includes a substrate formed of a semiconductor material, a source region and a drain region spaced apart from each other in the substrate and doped with an opposite conductivity type to that of the substrate, a channel region interposed between the source region and the drain region, an insulating layer disposed on the channel region and formed of an electrically insulating material, a first reference electrode disposed at an edge of the upper portion of the insulating layer and a second reference electrode disposed to be spaced apart from the insulating layer.

15 Claims, 5 Drawing Sheets

OTHER PUBLICATIONS

"Micro flow cell for blood gas analysis realizing very small sample volume": Authors: Shuichi Shoji, et al.; Sensors and Actuators B Chemical; vol. B08, No. 2, pp. 205-208 (May 1, 1992).

"A new pH-ISFET based dissolved oxygen sensor by employing electrolysis of oxygen"; Authors: Byung-Ki Sohn, et al.; Sensors and Actuators B; vol. 34, No. 1-3, pp. 435-440 (Aug. 1, 1996).

"Dynamic Behavior of ISFET-based Sensor-Actuator Systems"; Authors: W. Olthuis, et al.; Sensors and Actuators B; vol. 1, No. 1, pp. 416-420 (Jan. 1, 1990).

European Search Report Application No./ Patent No. 06124487.7-1240/ 1850124; Dated: Dec. 29, 2008.

* cited by examiner

FIELD EFFECT TRANSISTOR FOR DETECTING IONIC MATERIAL AND METHOD OF DETECTING IONIC MATERIAL USING THE SAME

This application claims priority to Korean Patent Application No. 10-2006-0037723, filed on Apr. 26, 2006, and all the benefits accruing therefrom under 35 U.S.C. §119, the contents of which are incorporated herein by reference in its entirety.

BACKGROUND OF THE INVENTION

1. Field of the Invention

The present invention relates to a field effect transistor for detecting ionic material and a method of detecting ionic material using the field effect transistor.

2. Description of the Related Art

Transistor base biosensors including transistors are sensors that electrically detect ionic material, for example, biomolecules. Biosensors are manufactured using semiconductor processes and relatively quickly convert electric signals. Therefore, research on biosensors has widely progressed.

U.S. Pat. No. 4,238,757 discloses the measuring of biological reactions using a field effect transistor ("FET") and relates to a biosensor capable of identifying an antigen-antibody reaction by detecting a current that varies due to a change in the surface charge concentration of a semiconductor inversion layer. This patent is directed toward a biosensor for detecting proteins. In U.S. Pat. No. 4,777,019, biological monomers are adsorbed onto the surface of a gate, and hybridization between the biological monomers and complementary monomers is measured using a FET.

U.S. Pat. No. 5,846,708 discloses a method of identifying hybridization using a charged coupled device ("CCD"). In this method, hybridization can be identified using a phenomenon of bonded biomolecules absorbing light. In U.S. Pat. Nos. 5,466,348 and 6,203,981, a circuit comprising a thin film transistor ("TFT") is used and a signal-to-noise ratio is improved.

A FET used as a biosensor lowers costs and requires less time than other conventional methods. In addition, a FET can be easily applied to integrated circuits ("IC")/microelectrical mechanical systems ("MEMS") processes.

FIG. 1 is a schematic diagram of a conventional FET for detecting ionic material. Referring to FIG. 1, a source 12 and a drain 13 are respectively formed in side portions of a substrate 11 doped with an n-or p-type material. The source 12 and the drain 13 are doped with an opposite conductivity type to that of the substrate 11. A channel 15 is interposed between the source 12 and the drain 13 and an insulating layer 14 contacting the source 12 and the drain 13 is formed on the substrate 11. A reference electrode 16 is formed above the insulating layer 14 and a constant voltage is applied to the reference electrode 16.

The size of the sensor including the FET is on the scale of microns, while the size of the reference electrode 16 is on the scale of millimeters. Therefore, it is difficult to reduce the overall size of the sensor.

On the other hand, U.S. Pat. No. 4,269,682 discloses a system including a measuring unit and a reference ejectrode, both having an insulating gate FET, and a pseudo reference electrode which applies bias to each FET and immobilizes electric potential of an electrolyte solution.

In the case of a metal electrode to which the system above is applied, voltage is very unstable. Therefore, in order to eliminate noise, gradation measurement may be performed using a reference FET.

Conventional FETs for detecting ionic material have relatively large scattering during their manufacture. Therefore, when similar samples are detected using these FETs, there is wide variation in measured electrical values. Accordingly, electrical values are measured using a large number of array FETs and then, the values are filtered and averaged to select and use good data.

BRIEF SUMMARY OF THE INVENTION

An exemplary embodiment provides a field effect transistor ("FET") for detecting ionic material, which can be miniaturized, and having improved scattering between a plurality of the FET devices so as to accurately detect ionic material using one or a small number of the FET devices and having an increased signal-to-noise ratio.

An exemplary embodiment provides a microflow apparatus for detecting ionic material, which can be miniaturized, and having improved scattering between the FET devices so as to accurately detect ionic material using one or a small number of the FET devices and having an increased signal-to-noise ratio.

An exemplary embodiment provides a method of detecting presence of concentration of ionic material easily and accurately.

In an exemplary embodiment, there is provided a field effect transistor for detecting ionic material. The field effect transistor includes a substrate formed of a semiconductor material, a source region and a drain region spaced apart from each other in the substrate and doped with an opposite conductivity type to that of the substrate, a channel region interposed between the source region and the drain region, an insulating layer disposed on the channel region and formed of an electrically insulating material, a first reference electrode disposed at an edge of the upper portion of the insulating layer and a second reference electrode disposed to be spaced apart from the insulating layer.

In an exemplary embodiment the field effect transistor may further include a separation layer disposed on the source region, the drain region and the first reference electrode and formed of an electrically insulating material.

In an exemplary embodiment the second reference electrode may be disposed on the separation layer.

In an exemplary embodiment the insulating layer may be disposed on portions of the source region and the drain region.

In an exemplary embodiment the electrically insulating material may be silicon dioxide, silicon nitride or metal oxide.

In an exemplary embodiment the source region and the drain region may be doped with a p-type material when the substrate is doped with n-type material. Alternatively, the source region and the drain region may be doped with an n-type material when the substrate is doped with a p-type material.

In an exemplary embodiment the first reference electrode may be formed of one of polysilicon, Al, Pt, Au and Cu.

In an exemplary embodiment the second reference electrode may be formed of one of platinum and Ag/AgCl.

In an exemplary embodiment the ionic material may be a biomolecule. The biomolecule may be one of nucleic acid and protein.

In an exemplary embodiment the nucleic acid may be selected from the group consisting of DNA, RNA, PNA, LNA and a hybrid thereof. The protein may be selected from the group consisting of an enzyme, a substrate, an antigen, an antibody, a ligand, an aptamer and a receptor.

In an exemplary embodiment there is provided a microflow apparatus including the field effect transistor for detecting ionic material. The field effect transistor may include a substrate formed of a semiconductor material, a source region and a drain region spaced apart from each other in the substrate and doped with an opposite conductivity type to that of the substrate, a channel region interposed between the source region and the drain region, an insulating layer disposed on the channel region and formed of an electrically insulating material, a first reference electrode disposed at an edge of the upper portion of the insulating layer and a second reference electrode disposed to be spaced apart from the insulating layer.

In an exemplary embodiment the field effect transistor may be formed in a micro channel of the microflow apparatus.

In an exemplary embodiment the substrate of the field effect transistor may be an inner surface of the micro channel.

In an exemplary embodiment there is provided a method of detecting ionic material. The method includes providing a sample solution used to detect the presence or concentration of ionic material to the insulating layer of a field effect transistor for detecting ionic material and measuring electric signal changes of the field effect transistor. The field effect transistor may include a substrate formed of a semiconductor material, a source region and a drain region spaced apart from each other in the substrate and doped with an opposite conductivity type to that of the substrate, a channel region interposed between the source region and the drain region, an insulating layer disposed on the channel region and formed of an electrically insulating material, a first reference electrode disposed at an edge of the upper portion of the insulating layer and a second reference electrode disposed to be spaced apart from the insulating layer.

In an exemplary embodiment the method may further include applying a constant or different voltage to each of the first and second reference electrodes of the field effect transistor before providing the sample solution.

In an exemplary embodiment the sample solution may be also provided to the first reference electrode and the second reference electrode of the field effect transistor, in addition to the insulating layer.

In an exemplary embodiment an electric signal of the field effect transistor may be one of source-drain current and voltage.

In an exemplary embodiment the nucleic acid may be one of a PCR product and a refined product thereof.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
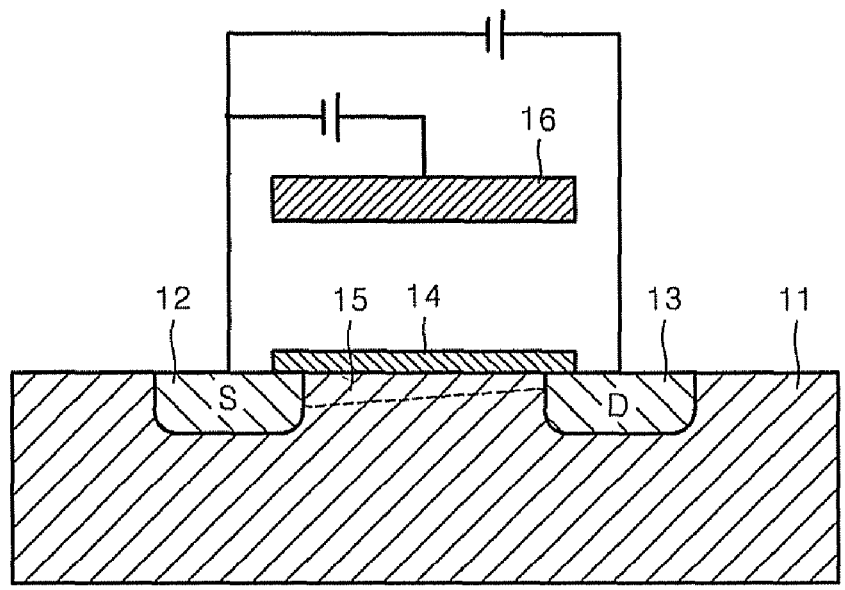
FIG. 1 is a schematic diagram of a conventional field effect transistor for detecting ionic material of the prior art.

The invention is described more fully hereinafter with reference to the accompanying drawings, in which exemplary embodiments of the invention are shown. This invention may, however, be embodied in many different forms and should not be construed as limited to the exemplary embodiments set forth herein. Rather, these embodiments are provided so that this disclosure will be thorough and complete, and will fully convey the scope of the invention to those skilled in the art. In the drawings, the size and relative sizes of layers and regions may be exaggerated for clarity.

It will be understood that when an element or layer is referred to as being "on" or "connected to" another element or layer, the element or layer can be directly on or connected to another element or layer or intervening elements or layers. In contrast, when an element is referred to as being "directly on" or "directly connected to" another element or layer, there are no intervening elements or layers present. Like numbers refer to like elements throughout. As used herein, the term "and/or" includes any and all combinations of one or more of the associated listed items.

It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Spatially relative terms, such as "above" and "upper" and the like, may be used herein for ease of description to describe the relationship of one element or feature to another element(s) or feature(s) as illustrated in the figures. It will be understood that the spatially relative terms are intended to encompass different orientations of the device in use or operation, in addition to the orientation depicted in the figures. For example, if the device in the figures is turned over, elements described as "above" or "upper" relative to other elements or features would then be oriented "below" the other elements or features. Thus, the exemplary term "above" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the invention are described herein with reference to cross-section illustrations that are schematic illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing.

For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of the invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this invention belongs.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Hereinafter, the present invention will be described more fully with reference to the accompanying drawings, in which exemplary embodiments of the invention are shown.

Figure 2:
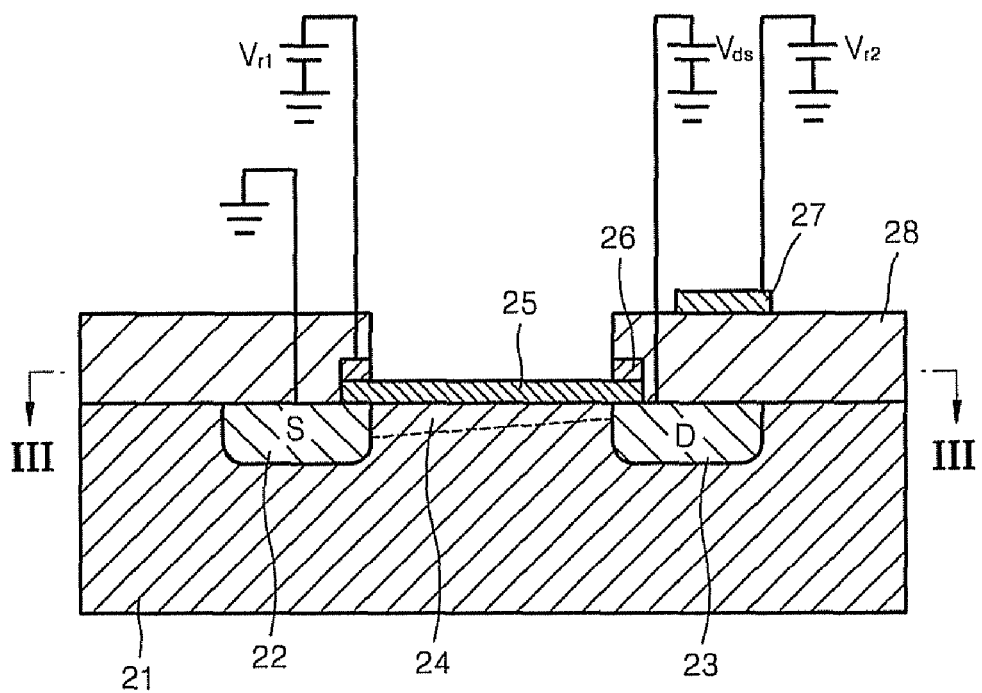
FIG. 2 is a schematic diagram of an exemplary embodiment of a field effect transistor for detecting ionic material according to the present invention.
Figure 3:
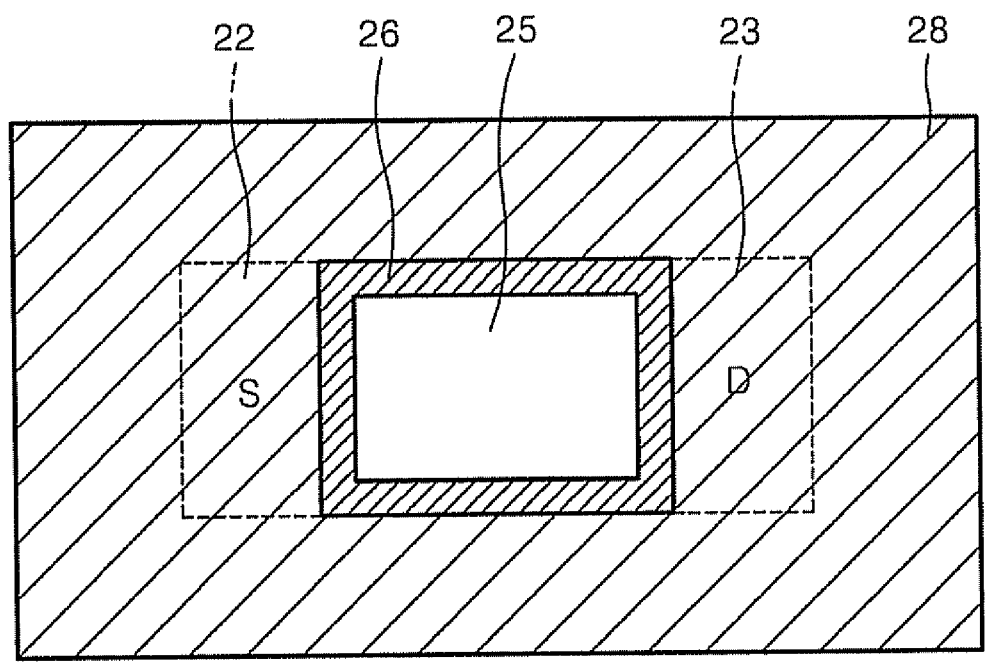
FIG. 3 is a plane cross-sectional view of the field effect transistor for detecting ionic material of FIG. 2 taken along line III-III of FIG. 2, according to the present invention.

FIG. 2 is a schematic diagram of an exemplary embodiment of a field effect transistor ("FET") for detecting ionic material according to the present invention and FIG. 3 is a plane cross-sectional view of the FET for detecting ionic material of FIG. 2 taken along line III-III of FIG. 2.

Referring to FIGS. 2 and 3, the FET for detecting ionic material includes a substrate 21, a source region 22, a drain region 23, a channel region 24, an insulating layer 25, a first reference electrode 26, a second reference electrode 27 and a separation layer 28.

In an exemplary embodiment, the substrate, 21 may be formed of a semiconductor material. In one exemplary embodiment, the semiconductor material may be Si or Ge.

The source region 22 and the drain region 23 disposed in the substrate 21 are spaced apart from each other and doped with an opposite conductivity type to that of the substrate 21. In one exemplary embodiment, when the substrate 21 is doped with an n-type material, the source region 22 and the drain region 23 may be doped with a p-type material, respectively, p-channel metal-oxide semi-conductor field-effect transistor ("PMOS-FET"). In an alternative embodiment, when the substrate 21 is doped with a p-type material, the source region 22 and the drain region 23 may be doped with a n-type material, respectively, n-type metal oxide semiconductor field-effect transistor ("NMOS-FET").

The source region 22 provides a carrier, such as a free electron or a hole (not shown). The carrier provided by the source region 22 reaches the drain region 23.

A constant voltage can be applied to the source region 22, such as a ground voltage. In an exemplary embodiment, another constant voltage ($Vd_s$) can be applied to the drain region 23.

The channel region 24 is formed in the substrate 21 and is interposed between the source region 22 and the drain region 23 as illustrated in FIG. 2. The carrier, such as a free electron or a hole, passes through the channel region 24.

The insulating layer 25 is disposed on the channel region 24. In an exemplary embodiment, the insulating layer 25 can be disposed on portions of the source region 22 and the drain region 23.

The insulating layer 25 is formed of an electrically insulating material. The electrically insulating material may be any of a number of materials on which biomolecules are not immobilized. Materials for the insulating layer may include, but are not limited to, silicon dioxide, silicon nitride or metal oxide. In exemplary embodiments, an additional layer (not shown) formed of a material on which biomolecules are not immobilized may be disposed on the insulating layer 25.

The first reference electrode 26 is disposed at an edge, such as the peripheral edge, of an upper portion of the insulating layer 25. As illustrated in FIG. 3, the first reference electrode 26 has a hole or opening substantially in the center thereof, exposing the insulating layer 25. As in the illustrated embodiment, the opening of the first electrode is substantially rectangular, but the shape of is not particularly restricted thereto. A constant voltage ($V_{r1}$) can be applied to the first reference electrode 26.

The first reference electrode 26 may be formed of any of a number of conductive materials, such as polysilicon, Al, Pt, Au, or Cu.

The first reference electrode 26 may be formed using various methods. In one exemplary embodiment, the first reference electrode 26 can be manufactured using an etching method. The etching method may be performed by etching from a passivation layer to a gate electrode layer until the edge portion of the gate electrode layer is left. The passivation layer is disposed on an upper portion of a FET.

The FET of the illustrated embodiment including the first reference electrode 26, may significantly reduce scattering of devices and significantly improve a signal-to-noise ratio.

Referring to FIGS. 2 and 3, the separation layer 28 is disposed on the source region 22, the drain region 23 and the first reference electrode 26. The separation layer 28 may be formed of an electrically insulating material.

The electrically insulating material for the separation layer 28 may be any of a number of materials on which biomolecules are not immobilized, such as, silicon dioxide, silicon nitride, or metal oxide.

The second reference electrode 27 is disposed on the separation layer 28. When the second reference electrode 27 is disposed on the separation layer 28, the FET can be miniaturized. The second reference electrode 27 can be formed of any of a number of conductive materials, such as, platinum or Ag/AgCl. A constant voltage ($V_{r2}$) can also be applied to the second reference electrode 27.

In an alternative exemplary embodiment, the second reference electrode 27 may be spaced apart from the insulating layer 25 and disposed in the space in a chamber (not illustrated) or may be disposed on a sidewall that defines the chamber.

The FET for detecting ionic material of the illustrated embodiment can accurately detect ionic material.

The types of ionic material are not particularly restricted, and may include, but are not limited to, ionic atoms, ionic molecules, or biomolecules. The biomolecules may be nucleic acid or protein.

The nucleic acid indicates various nucleic acids, similar nucleic acids, or a hybrid thereof and can be selected from the group consisting of deoxyribonucleic acid ("DNA"), ribonucleic acid ("RNA"), Peptide Nucleic Acid ("PNA"), Locked Nucleic Acid ("LNA"), and a hybrid thereof. In addition, the nucleic acid may be oligonucleotide or a polymerase chain reaction ("PCR") product, such as, a refined product of a PCR product.

The protein can be selected from the group consisting of an enzyme, a substrate, an antigen, an antibody, a ligand, an aptamer and a receptor.

As an exemplary embodiment, a microflow apparatus including the FET of the illustrated embodiment is provided.

In the microflow apparatus (not shown) for detecting ionic material, an inlet, an outlet, and a reaction chamber are connected via a micro channel through which fluid flows. The microflow apparatus may further include a micro pump, a micro valve, a micro mixer, and a micro filter, in addition to the micro channel. The micro pump transfers fluid, the micro valve controls fluid transfer, the micro mixer mixes fluid, and the micro filter filters transferred fluid.

The microflow apparatus also includes a plurality of chambers which can perform one or more processes such as cell counting, cell sorting, DNA detecting, and PCR amplifying/detecting to conduct biological analysis, and the chambers are sequentially connected via a channel through which fluid flows.

The FET as in the illustrated embodiment may be formed in the micro channel. The substrate of the FET may be the inner surface of the micro channel and the second reference electrode of the FET may be separated from the insulating layer to be formed in the inner surface of the micro channel.

As an exemplary embodiment, a method of detecting ionic material using the FET of the illustrated embodiment is provided.

In order to detect ionic material, a constant voltage is applied to each of the first and second reference electrodes of the FET before providing a sample solution for detecting presence or concentration of ionic material. A constant voltage may be applied between the source region and drain region of the FET or the source region and drain region can be set so that a constant current flows therebetween. In an alternative embodiment, a different voltage may be applied to each of the first and second reference electrodes of the FET before providing a sample solution for detecting presence or concentration of ionic material.

Next, the sample solution is provided to the insulating layer of the FET for detecting ionic material. The sample solution may be provided to the first and second reference electrodes, and/or in addition to the insulating layer.

The types of ionic material are not particularly restricted, and may include, but are not limited to, ionic atoms, ionic molecules, or biomolecules. The biomolecules may be nucleic acid or protein.

The nucleic acid indicates various nucleic acids, similar nucleic acids, or a hybrid thereof and can be selected from the group consisting of DNA, RNA, Peptide Nucleic Acid ("PNA"), Locked Nucleic Acid ("LNA"), and a hybrid thereof. In addition, the nucleic acid may be oligonucleotide or a PCR product, such as, a refined product of a PCR product.

The protein can be selected from the group consisting of an enzyme, a substrate, an antigen, an antibody, a ligand, an aptamer, and a receptor.

Next, electric signal changes of the FET are measured. The electric signal of the FET may be a source-drain current or voltage. When a constant voltage is applied between the source region and the drain region, the electric signal may be the source-drain current. When the source region and drain region is set for a constant current to flow therebetween, the electric signal may be voltage.

An exemplary embodiment of the method of detecting ionic material may include detecting a PCR product of nucleic acid. If a target biomolecule exists in a sample, a PCR may be performed. If a target biomolecule do not exist in a sample, a PCR may not be performed. Therefore, since PCR products can be detected, presence or concentration of the target biomolecule in the sample can be detected.

The present invention will be described in greater detail with reference to the following examples. The following examples are for illustrative purposes only and are not intended to limit the scope of the invention.

EXAMPLE 1

Manufacture of FET

A FET device used in the present invention was a conventional FET device manufactured by X-FAB Semiconductor Foundries (Germany). This device had 192 FETs, all having the same structure and arranged in an array shape (12×16). The FET device was manufactured using a complementary metal-oxide semi-conductor ("CMOS") process and equipment, both owned by X-FAB Semiconductor Foundries. CMOS manufacturing processes slightly differ according to company, and thus, a detailed description thereof is omitted herein for brevity.

The upper surface of the FET device manufactured as described above was etched as illustrated in FIGS. 2 and 3. In other words, the passivation layer and the gate electrode layer of each FET were removed to expose a silicon oxide layer, that is, the insulating layer 25. As clearly illustrated in FIG. 3, instead of etching the entire gate electrode layer, the middle portion of the gate electrode layer was etched to leave the edge portion thereof as the first reference electrode 26.

Next, an external second reference electrode spaced apart from the insulating layer was formed and an internal second reference electrode was formed on the separation layer. The external and internal second reference electrodes were formed of platinum and a constant standard voltage was applied thereto. In exemplary embodiments, one of the external second reference electrode or the internal second reference electrode can be formed, however, for experimental convenience, both the external second reference electrode and the internal second reference electrode were formed.

Then, two chambers including the exposed insulating layer, the first reference electrode, and the external and internal second reference electrodes were formed. Each chamber included 192 FETs.

While the manufacturing process described above was performed or when the manufacturing process described above was completed, washing and drying processes were performed. That is, the surface of the FET including the exposed silicon oxide layer was carefully washed using pure acetone and water and then dried. A wet station used in a semiconductor manufacturing process was used in the washing process. When the washing process was completed, the drying process was performed using a spin drying method.

EXPERIMENTAL EXAMPLE 1

Detecting Solution Using FET

The two chambers each including the FET device manufactured according to Example 1 constituted a sensing chamber and a reference chamber.

0.01 millimole (mM) of a phosphate buffer ("PB") solution (pH 5.88) continuously flowed in and out of the reference chamber. 0.01 mM of a PB solution (pH 5.88) firstly flowed into the sensing chamber, as in the reference chamber, and then, solutions containing different ionic materials, for example, 0.1 mM of a NaOAc solution (pH 4.72) and 0.01 mM of PB solution (pH 6.08), alternately flowed in and out of the sensing chamber.

A constant voltage was continuously applied to the source and drain regions of the FET included in the reference chamber and the sensing chamber, while the first reference electrode and the external and internal second reference electrodes were on and off.

The source and drain current according to inflow of solutions containing different pHs and the on-off state of the first reference electrode and the external and internal second reference electrodes was measured.

Figure 4:
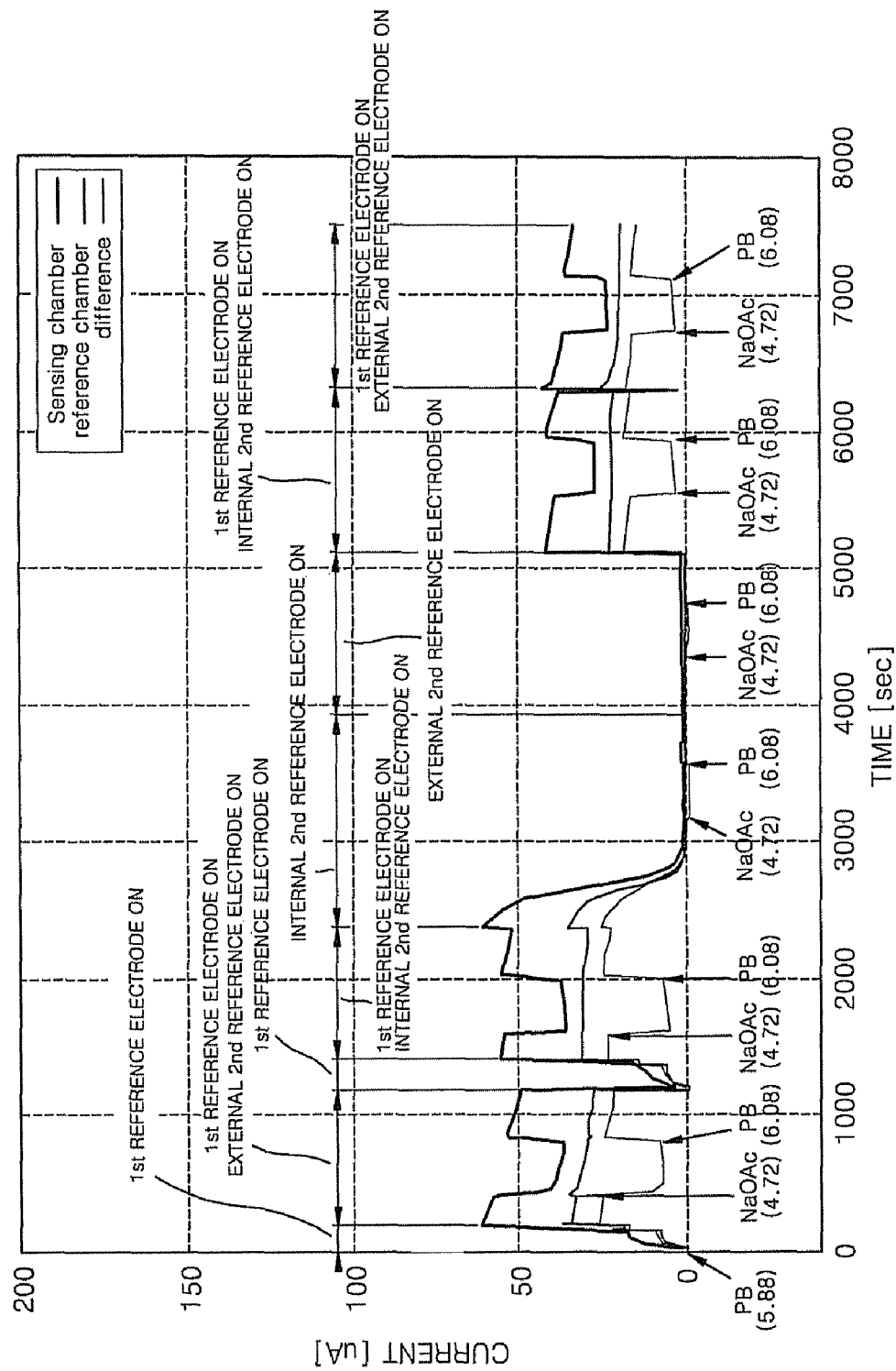
FIG. 4 is a graph showing overall average current values based on an inflow of solutions having different pH values and an on-off state of reference electrodes used in an experimental example of the present invention.

FIG. 4 is a graph showing overall average current values according to inflow of solutions containing different pHs and the on-off state of the first reference electrode and the external and internal second reference electrodes used in Experimental Example 1.

Referring to FIG. 4, while 0.01 mM of a PB solution (pH 5.88) firstly flowed into the first reference electrode and a voltage of 1.8 V was applied to the external second reference electrode, the first reference electrode was on.

The voltage applied to the first reference electrode was increased from 0 V to 1.9 V. Then, a voltage of 1.9 V was continuously applied to the first reference electrode and voltages of 1.9 V and 2.0 V were sequentially applied to the external second reference electrode. In this case, 0.1 mM of a NaOAc solution (pH 4.72) and 0.01 mM of a PB solution (pH 6.08) alternately flowed into the sensing chamber.

Next, the first reference electrode and the external second reference electrode were off and a voltage of 1.8 V was applied to the internal second reference electrode. Then the first reference electrode was on to increase a voltage from 0 V to 1.9 V. Next, while a voltage of 1.9 V was continuously applied to the first reference electrode, voltages of 1.9 V and 2.0 V were sequentially applied to the internal second reference electrode. In this case, 0.1 mM of a NaOAc solution (pH 4.72) and 0.01 mM of a PB solution (pH 6.08) alternately flowed in to the sensing chamber. The purpose of this experiment was to change the voltage of the first reference electrode when any one of the internal and external second reference electrodes was always on.

The potential of the solution could not be detected using the first reference electrode only and thus, both the first reference electrode and the external and internal second reference electrodes were used.

Next, the first reference electrode was off and a voltage of 2.0 V was continuously applied to the internal second reference electrode. In this case, 0.1 mM of a NaOAc solution (pH 4.72) and 0.01 mM of a PB solution (pH 6.08) alternately flowed into the sensing chamber. Then the internal second reference electrode was off and a voltage of 2.0 V was applied to the external second reference electrode to turn on the external second reference electrode. In this case, 0.1 mM of a NaOAc solution (pH 4.72) and 0.01 mM of a PB solution (pH 6.08) alternately flowed into the sensing chamber.

Next, the external second reference electrode was off and voltages of 1.9 V and 2.0 were applied to the first reference electrode and the internal second reference electrode, respectively, to turn on the first reference electrode and the internal second reference electrode. In this case, 0.1 mM of a NaOAc solution (pH 4.72) and 0.01 mM of a PB solution (pH 6.08) alternately flowed into the sensing chamber.

Next, a voltage of 1.9 V was continuously applied to the first reference electrode, the internal second reference electrode was off, and a voltage of 2.0 V was applied to the external second reference electrode to turn on the external second reference electrode. In this case, 0.1 mM of a NaOAc solution (pH 4.72) and 0.01 mM of a PB solution (pH 6.08) alternately flowed into the sensing chamber.

As illustrated in FIG. 4, when only the internal and the external second reference electrodes were on, currents measured at the sensing chamber and the reference chamber were nearly 0 A and thus, were hardly distinguished. When voltage was applied after both the first reference electrode and the internal or external second reference electrode were on at the same time, the reference electrodes were reacted with the solutions containing different pHs and thus, current values changed efficiently.

EXPERIMENTAL EXAMPLE 2

Detecting PCR Products Using FET

An experiment was performed to identify whether the FET manufactured according to Example 1 could detect PCR products.

In order to do so, a solution including PCR products, a washing solution, and a negative control ("NTC") solution were alternately injected to a FET based sensor.

In order to obtain the PCR products, *Staphylococcus aureus* bacteria template was used to perform a PCR amplifying process. The base sequence of forward and reverse primer used in the process was 5'-(TAG CAT ATC AGA AGG CAC ACC C)-3' (SEQ ID NO: 1) and 5'-(ATC CAC TCA AGA GAG ACA ACA TT)-3' (SEQ ID NO: 2), respectively. The PCR products obtained after the PCR amplifying process had the size of 240 base pairs (bp). In addition, the concentration of PCR products was diluted to be 5 nanograms per microliter (ng/µl) using phosphate buffer. The pH of the phosphate buffer containing PCR products was 5.49.

0.01 mM of phosphate buffer (pH 6.02) was used as the washing solution.

The NTC solution contains no template during the PCR process and thus, production of the PCR products was obstructed. Therefore, the NTC solution was used to identify an obstruction effect of materials other than the PCR products. The PCR process performed was same as above and the only difference was that template was not added. When the PCR process was completed, PCR amplification did not occur and thus, the concentration of the PCR products was unknown. Such a PCR process was performed on the basis that PCR was not performed when target DNA did not exist in a sample. The pH of the NTC solution was 5.16.

Figure 5:
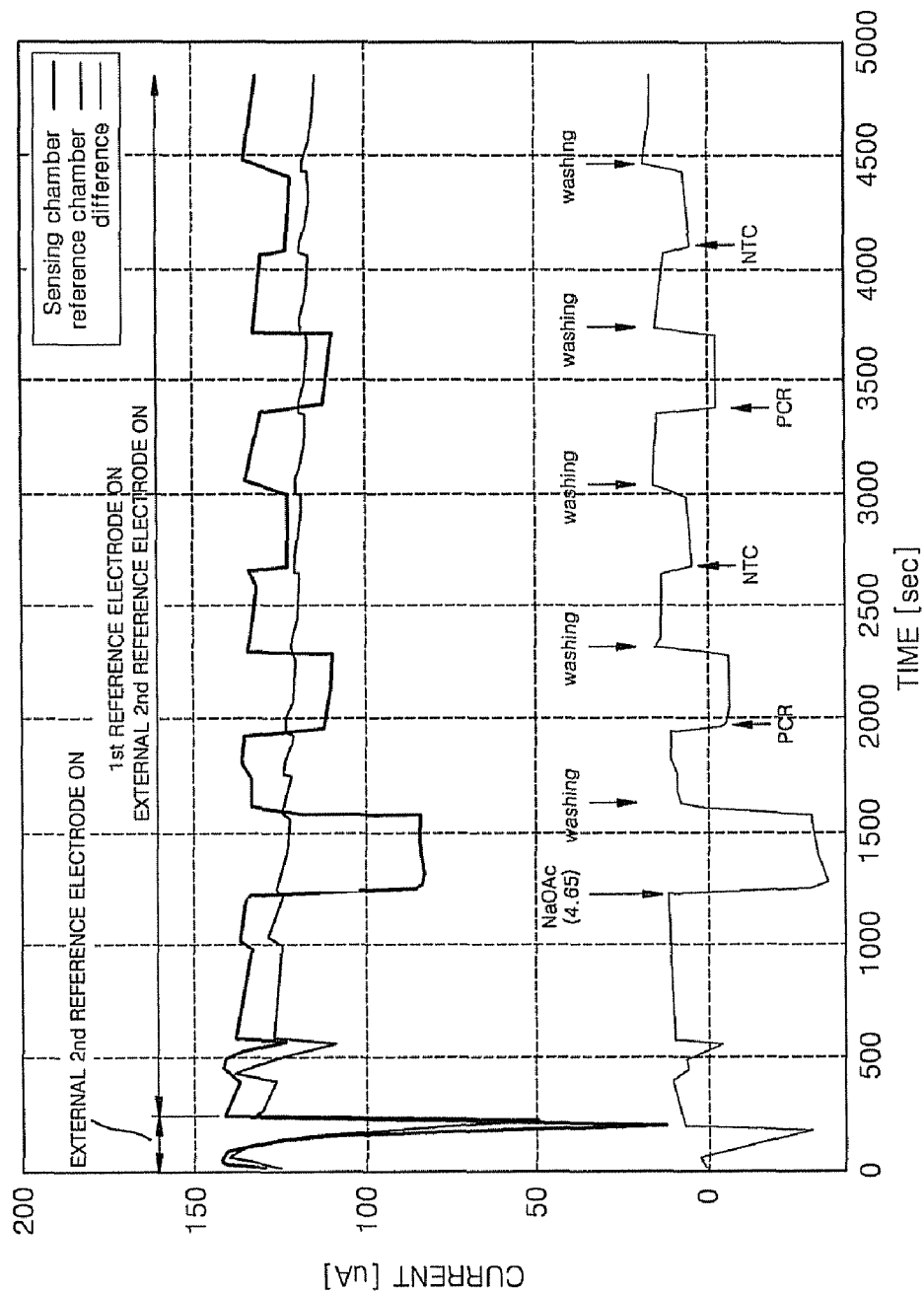
FIG. 5 is a graph showing overall average current values of an experimental example when a solution including PCR product, a washing solution and a NTC solution were alternately injected to the FET manufactured according to Example 1.

FIG. 5 is a graph showing overall average current values when the solution including PCR products, the washing solution, and the NTC solution used in Experimental Example 2 were alternately injected to the FET.

Referring to FIG. 5, when the solution including PCR products, the washing solution and the NTC solution were alternately injected, current variation values were clearly distinguished. Therefore, the FET of the illustrated embodiment can be efficiently used to detect PCR products.

EXPERIMENTAL EXAMPLE 3

Detecting pH Using FET

An experiment was performed to identify whether the FET manufactured according to Example 1 could detect pH.

In order to do so, solutions having pHs of 3, 6, and 9 were injected to a FET based sensor to measure current values.

Figure 6:
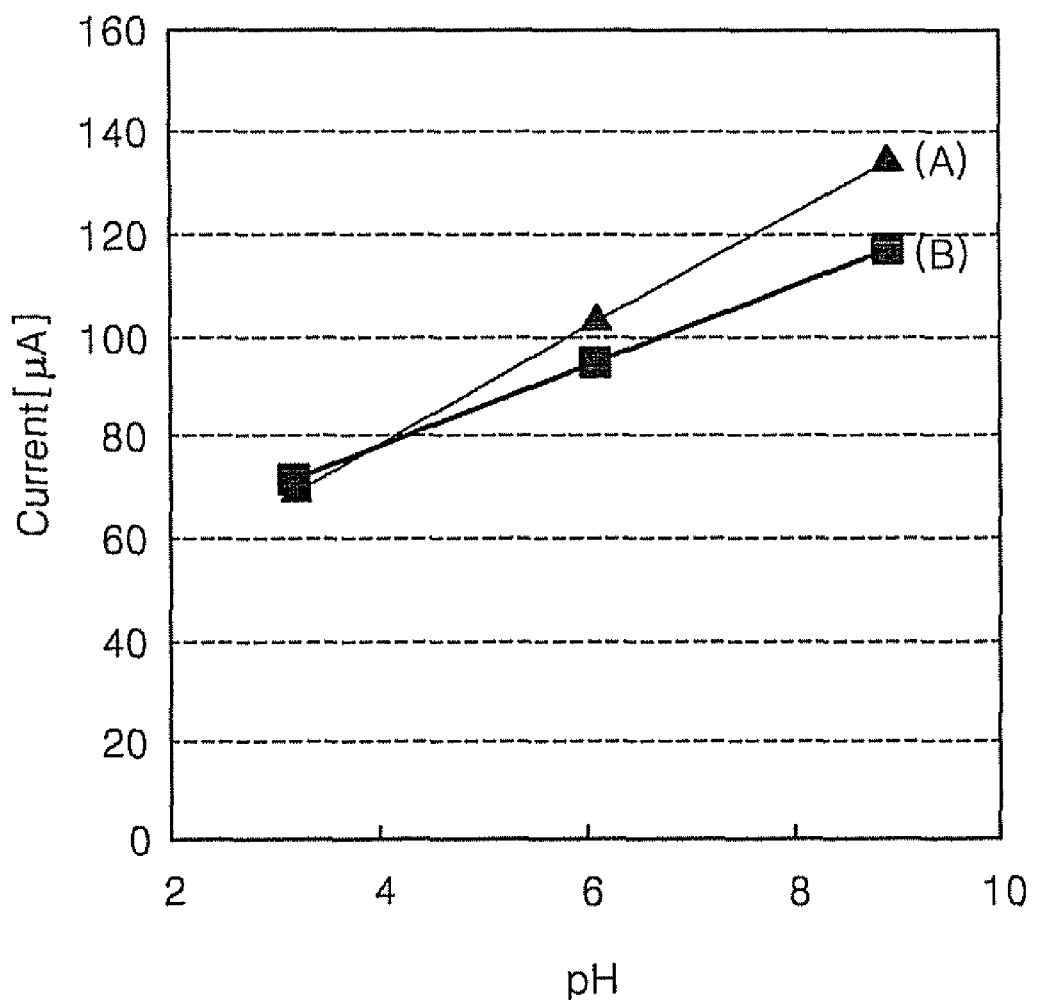
FIG. 6 is a graph showing current values of an experimental example when solutions having different pHs were injected to the FET manufactured according to Example 1.

FIG. 6 is a graph showing current values when solutions having different pHs used in Experimental Example 3 were injected to the FET based sensor.

Referring to FIG. 6, line (A) (e.g. --▲--) indicates when voltages of 1.8 V and 1.9 V were applied to the first reference electrode and the external second reference electrode, respectively and line (B) (e.g. --■--) indicates when voltages of 1.6 V and 1.9 V were applied to the first reference electrode and the external second reference electrode, respectively.

As illustrated in FIG. 6, current changes linearly according to the pHs of the solution used to measure the current. Therefore, the FET of the illustrated embodiment can be efficiently used to detect pH.

As described above, the FET and the microflow apparatus of the illustrated embodiments can improve scattering between the FET devices so as to accurately detect ionic material using one or a small number of the FET devices, significantly increase a signal-to-noise ratio and allow for the miniaturization of the devices. The FET and the microflow apparatus can be used to easily and accurately detect the presence or concentration of ionic material.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A field effect transistor for detecting ionic material, the field effect transistor comprising:
    a substrate formed of a semiconductor material;
    a source region and a drain region spaced apart from each other in the substrate and doped with an opposite conductivity type to that of the substrate;
    a channel region interposed between the source region and the drain region;
    an insulating layer disposed on the channel region and formed of an electrically insulating material;
    a first reference electrode disposed at an edge of the upper portion of the insulating layer; wherein the first reference electrode has an opening in the center thereof, exposing the insulating layer, and
    a second reference electrode disposed upon an upper surface of a separation layer and in intimate contact with the separation layer; the separation layer being disposed upon the source region, the drain region and the first reference electrode such that a lowest surface of the second electrode lies above a highest surface of the first electrode; wherein the separation layer comprises an electrically insulating material.

2. The field effect transistor of claim 1, further comprising a separation layer disposed on the source region, the drain region and the first reference electrode and formed of an electrically insulating material.

3. The field effect transistor of claim 2, wherein the second reference electrode is disposed on the separation layer.

4. The field effect transistor of claim 1, wherein the insulating layer is disposed on portions of the source region and the drain region.

5. The field effect transistor of claim 1, wherein the electrically insulating material is silicon dioxide, silicon nitride, or metal oxide.

6. The field effect transistor of claim 1, wherein the source region and the drain region are doped with a p-type material when the substrate is doped with n-type material.

7. The field effect transistor of claim 1, wherein the source region and the drain region are doped with an n-type material when the substrate is doped with a p-type material.

8. The field effect transistor of claim 1, wherein the second reference electrode is formed of one of platinum and Ag/AgCl.

9. The field effect transistor of claim 1, wherein the ionic material is a biomolecule.

10. The field effect transistor of claim 9, wherein the biomolecule is one of nucleic acid and protein.

11. The field effect transistor of claim 10, wherein the nucleic acid is selected from the group consisting of DNA, RNA, PNA, LNA and a hybrid thereof.

12. The field effect transistor of claim 10, wherein the protein is selected from the group consisting of an enzyme, a substrate, an antigen, an antibody, a ligand, an aptamer, and a receptor.

13. A microflow apparatus comprising the field effect transistor for detecting ionic material of claim 1.

14. The microflow apparatus of claim 13, wherein the field effect transistor is formed in a micro channel of the microflow apparatus.

15. The microflow apparatus of claim 13, wherein the substrate of the field effect transistor is an inner surface of a micro channel of the microflow apparatus.

* * * * *

SEQUENCE LISTING

```
<160> NUMBER OF SEQ ID NOS: 2

<210> SEQ ID NO 1
<211> LENGTH: 22
<212> TYPE: DNA
<213> ORGANISM: Artificial Sequence
<220> FEATURE:
<223> OTHER INFORMATION: forward primer

<400> SEQUENCE: 1
tagcatatca gaaggcacac cc                                              22

<210> SEQ ID NO 2
<211> LENGTH: 23
<212> TYPE: DNA
<213> ORGANISM: Artificial Sequence
<220> FEATURE:
<223> OTHER INFORMATION: reverse primer

<400> SEQUENCE: 2
atccactcaa gagagacaac att                                             23
```